United States Patent [19]
Schmieding et al.

[11] Patent Number: 5,683,401
[45] Date of Patent: *Nov. 4, 1997

[54] METHOD AND APPARATUS FOR INSTALLING A SUTURE ANCHOR THROUGH A HOLLOW CANNULATED GRASPER

[75] Inventors: Reinhold Schmieding, Naples, Fla.; Stefan Krupp, Munich, Germany

[73] Assignee: Arthrex, Inc., Naples, Fla.

[*] Notice: The term of this patent shall not extend beyond the expiration date of Pat. No. 5,466,243.

[21] Appl. No.: 552,694

[22] Filed: Nov. 3, 1995

Related U.S. Application Data

[63] Continuation of Ser. No. 197,829, Feb. 17, 1994, Pat. No. 5,466,243.
[51] Int. Cl.⁶ .................................................. A61B 17/00
[52] U.S. Cl. ........................... 606/104; 606/205; 606/232
[58] Field of Search .................................. 606/232, 104, 606/72–75, 187, 205–208; 81/52, 53.2, 451, 57.13, 57.14

[56] References Cited

U.S. PATENT DOCUMENTS

| | | | |
|---|---|---|---|
| 734,204 | 7/1903 | Voss | 81/451 |
| 3,892,232 | 7/1975 | Neufeld | 606/104 |
| 4,641,652 | 2/1987 | Hutterer et al. | 606/148 |
| 4,779,616 | 10/1988 | Johnson | 606/148 |
| 4,836,205 | 6/1989 | Barrett | 606/144 |
| 5,141,520 | 8/1992 | Goble et al. | 606/232 |
| 5,370,662 | 12/1994 | Stone et al. | 606/232 |
| 5,372,146 | 12/1994 | Branch | 606/232 |
| 5,374,270 | 12/1994 | McGuire et al. | 606/104 |
| 5,431,660 | 7/1995 | Burke | 606/104 |
| 5,520,700 | 5/1996 | Beyar et al. | 606/232 |

*Primary Examiner*—Jeffrey A. Schmidt
*Attorney, Agent, or Firm*—Ostrolenk, Faber, Gerb & Soffen

[57] ABSTRACT

An arthroscopic method and apparatus for implanting a suture fixation device or other appliance into tissue using a hollow cannulated grasper. Tissue at a repair site is secured with a hollow grasper. Suture material is appended to a suture anchor. The suture anchor or other appliance is attached to a device driver and installed through the hollow grasper into the repair site, where it is drilled into bone.

22 Claims, 3 Drawing Sheets

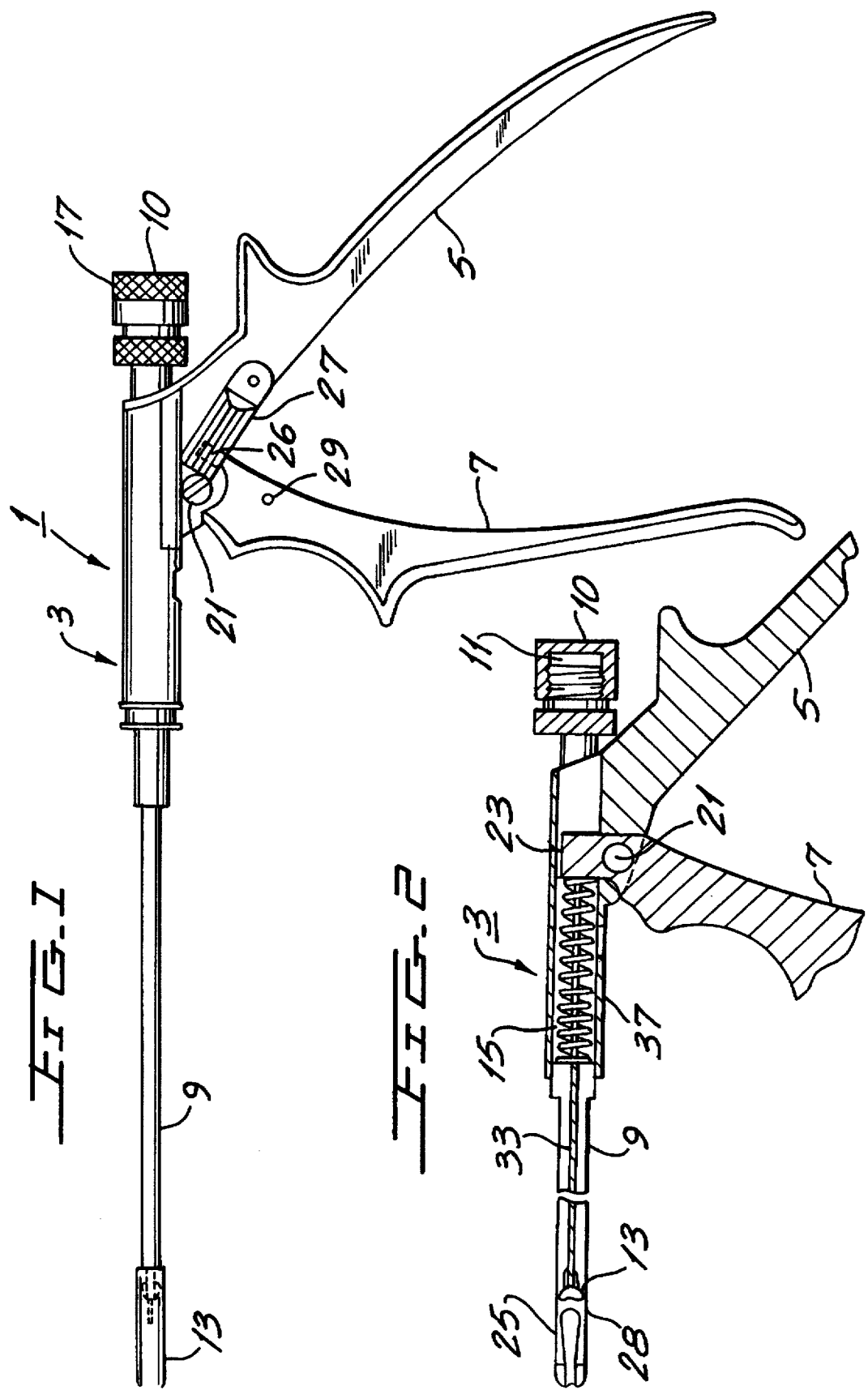

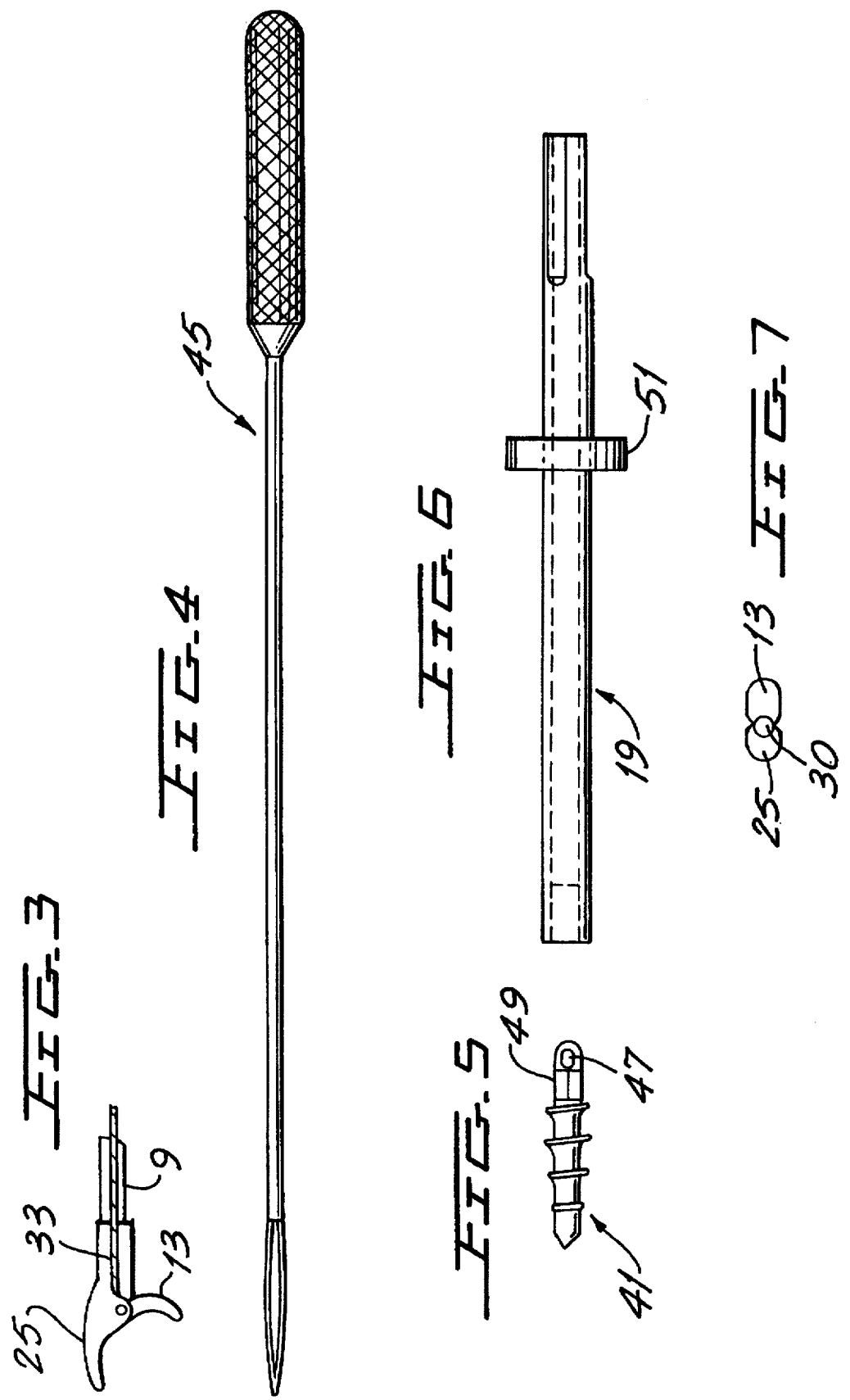

METHOD AND APPARATUS FOR INSTALLING A SUTURE ANCHOR THROUGH A HOLLOW CANNULATED GRASPER

This is a continuation of application Ser. No. 08/197,829, filed Feb. 17,1994, now U.S. Pat. No. 5,466,243.

BACKGROUND OF THE INVENTION

1. Field of the Invention

The present invention relates to an arthroscopic surgical method and apparatus for suture fixation, and specifically to an arthroscopic method and apparatus for installing a suture anchor through a hollow grasping means.

2. Brief Description of the Prior Art

Suture anchors are used in arthroscopic surgery to secure suture material to tissue. Various suture anchor assemblies have been developed. For example, U.S. Pat. No. 4,632,100to Somers et al. and U.S. Pat. No. 4,898,156to Gatturna et al. disclose suture anchors and tools for suture anchor installation. See also U.S. Pat. No. 4,899,743to Nicholson et al.

The devices of the above-mentioned patents are disadvantageous because they do not secure the anchor-delivering end of the driver at the tissue repair site while the suture anchor is driven into the repair tissue. In order to provide stabilization at the tissue site, many of the prior art devices require that the suture anchor be inserted into a pre-drilled hole, as in Gatturna et al. and Nicholson et al. Other prior art devices, such as the device taught by Somers, rely on the technical skill of the surgeon to screw, for example, a self-tapping suture anchor into bone.

Guiding small suture anchor pins and driving them into bone tissue can be excessively demanding, particularly, for example, in arthroscopic Bankart repair. Inserting suture anchors into the glenoid rim is technically formidable, making the procedure infeasible.

SUMMARY OF THE INVENTION

The present invention overcomes the above-noted disadvantages by providing a method and apparatus for installing a suture anchor or other appliance through a hollow cannulated grasper. The grasper secures tissue at the installation site, providing a sturdy guide-way through which suture anchors and other appliances can be delivered to a tissue repair site for implantation.

The method of the present invention for installing a suture anchor includes the steps of grasping tissue with a hollow grasper and introducing a threaded suture anchor to the tissue through the hollow grasper. Once the suture anchor is implanted, the hollow grasper is removed, leaving the suture anchor in place.

The depth of implantation can be controlled with a depth gauge or drill stop device. The method is repeated to effect further suture anchor installations.

By the method of the present invention, arthroscopic implantation of suture anchors is made simpler and more feasible due to increased stability at the tissue site during installation.

Other features and advantages of the present invention will become apparent from the following description of the invention which refers to the accompanying drawings.

BRIEF DESCRIPTION OF THE DRAWINGS

FIG. 1 is a left side elevation perspective of a preferred hollow grasper device utilized in accordance with the method of the present invention.

FIG. 2 is a cut away detail of the grasper and jaw assembly.

FIG. 3 is a partial side view of the grasper showing the jaw assembly in an open position.

FIG. 4 is a left side elevation perspective of a suture material threading device used with the apparatus and method of the present invention.

FIG. 5 is an enlarged left side elevation perspective of a preferred suture anchor used with the apparatus and method of the present invention.

FIG. 6 is an enlarged left side elevation perspective of a preferred suture fixation device driver used with the apparatus and method of the present invention.

FIG. 7 is a partial end view of the present invention showing the jaw assembly in a closed position.

DETAILED DESCRIPTION OF THE PREFERRED EMBODIMENT

Figure 8:
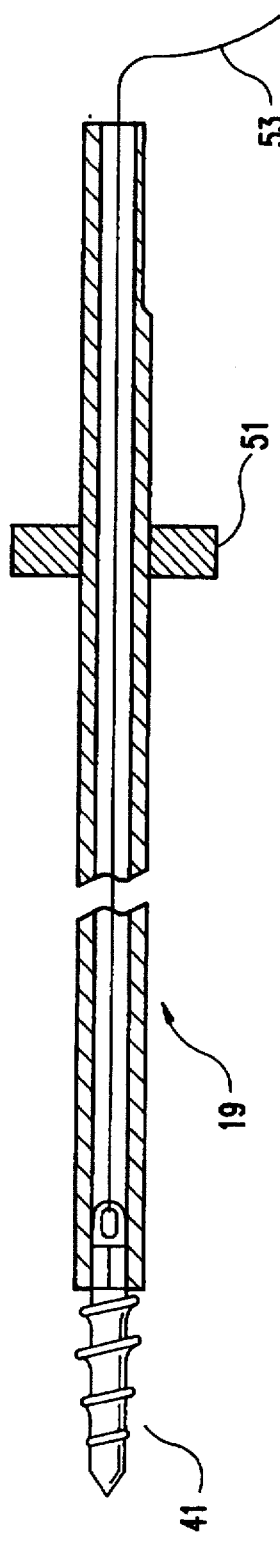
FIG. 8 is a cut-away view of an assembly for installing a suture anchor according to an embodiment of the present invention.

Referring to FIG. 1, the present invention relates to a hollow cannulated grasper 1 consisting of a handpiece 3 having a pistol grip 5, a trigger 7, an elongated, hollow barrel 9, a cap 10 encasing a fluid dam 11, and a moveable jaw 13.

As shown in FIG. 2, handpiece 3 includes a hollow portion 15. Cap 10, disposed at the back end of handpiece 3, includes knurls 17 on its outer surface which provide a grip for unscrewing the cap for removal of fluid dam 11 contained therein. Fluid dam 11 is formed of a replaceable, flexible material, such as rubber. A device driver 19 shown in FIG. 6, is designed to be pushed through a pair of cross-hatched slits (not shown) in the center of fluid dam 11. The rubber fits snugly around devices pushed through fluid dam 11 and inhibits back flow of body fluids during surgical procedures.

Trigger 7 is pivotally connected to the handpiece by pivot pin 21. The trigger 7 includes an extension 23 (FIG. 2) which projects into the hollow portion 15 of handpiece 3.

A barrel 9 is secured to the front end of handpiece 3. Barrel 9 includes a stationary jaw 25 disposed at its distal end. The distal end of barrel 9 also includes a moveable jaw 13 manipulated by the operator using trigger 7, as described in further detail below.

The grasper 1 is held in one hand using trigger 7 and pistol grip 5. The handpiece 3 can be grasped with the other hand to steady the instrument, if so desired.

Both the stationary jaw 25 and the moveable jaw 13 are provided with sharp tips 28 to assist in biting into the tissue. Tips 28 cooperate to form an opening 30, shown in FIG. 7, through which a suture anchor can pass when the jaws are closed.

In the operation of the device, the distal end of the grasper is positioned at the repair site against the tissue to be grasped. Moveable jaw 13 is advanced toward stationary jaw 25 by squeezing trigger 7 toward pistol grip 5. As trigger 7 moves inward by pivoting about pivot pin 21, extension 23 is urged against rod 33, advancing rod 33 forward toward the distal end of barrel 9 against the force of spring 37. When rod 33 is advanced forward, moveable jaw 13 pivots toward stationary jaw 25 to close the jaws. Once the appropriate section of tissue is isolated and grasped by jaws 13, 25, the trigger 7 may be locked in its closed position by rotating a latch 27 counterclockwise, such that a slot 26 in latch 27 is secured over a pin 29.

A threaded suture anchor 41 (FIG. 5) is then inserted through the device using device driver 19. To thread the suture anchor 41, appropriately sized suture is threaded through an eye 47 of suture anchor 41. Eye 47 and drive end 49 of suture anchor 41 are seated in device driver 19. Threading device 45 (FIG. 4) may be used to thread the suture through device driver 19.

Next, the threaded suture anchor and device driver are inserted through the fluid dam 11 of the cannulated grasper 1 and into the hollow barrel 9. When the device driver is fully inserted, the suture anchor 41 at the distal end thereof projects out through the end of the barrel and between the closed jaws into position at the tissue repair site.

A power drill is attached to the proximal end of driver 19. The suture anchor 41 is drilled through the closed jaws and into the repair site (e.g., the glenoid rim) in one maneuver. An adjustable drill depth guide stop 51 provides drilling depth control.

Once suture anchor 41 is in place, device driver 19 and cannulated grasper 1 are withdrawn from the repair site. The threaded suture anchor 41 is left in place for continuing the repair. Knots in the suture material may be tied using a knot pusher such as that described in U.S. Pat. No. 5,176,691. The installation procedure is repeated as necessary to install additional suture anchors.

Referring to FIG. 8, an assembly for installing suture anchor 41 is shown. The assembly includes device driver 19, suture anchor 41, and suture 53. Device driver 19 is an elongated, cannulated member having a distal end in which suture anchor 41 is received, and a proximal end for attachment to a power drill (not shown). Suture anchor 41 is threaded with suture 53. Adjustable depth stop 51 is an annular ring, for example, disposed slidably on device driver 19 near the proximal end thereof. Depth stop 51 is held in a selected position by friction, for example, between depth stop 51 and the outer surface of device driver 19. The position of the depth stop can be selected by the surgeon to mark an insertion depth for suture anchor 41.

Figure 9:
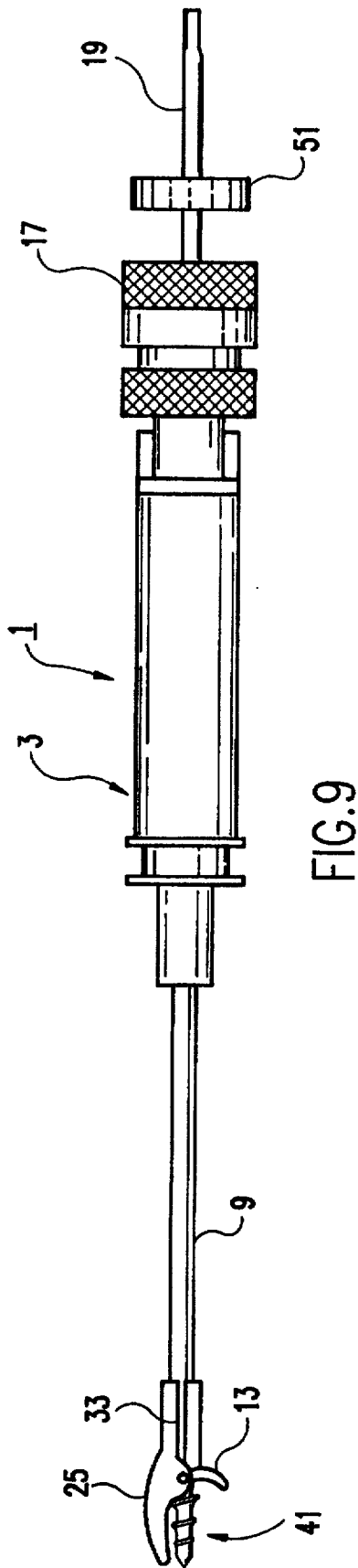
FIG. 9 is a top view of the hollow grasper according to an embodiment of the present invention with the assembly of FIG. 8 inserted through the hollow grasper for installation of a suture anchor.

Referring to FIG. 9, driver 19 is shown inserted within hollow grasper 1. Depth stop 51 contacts the proximal end of the hollow grasping means to indicate the depth of installation of suture anchor 41 into bone.

Although the present invention has been described in relation to particular embodiments thereof, many other variations and modifications and other uses will become apparent to those skilled in the art. It is preferred, therefore, that the present invention be limited not by the specific disclosure herein, but only by the appended claims.

What is claimed is:

1. An assembly for installing a suture anchor threaded with suture through tissue and into bone the assembly comprising:

(a) a suture;

(b) a suture anchor having a distal end, a proximal end, an outer thread diameter, and an eye, the suture being threaded through the eye; and (c) a device driver for engaging the suture anchor and comprising an elongated cannulated unitary tube having a distal end for receiving the suture anchor and a proximal end for attachment to a drill, the unitary tube having a substantially constant outer diameter and a complete cylindrical body from the distal end to the proximal end, the outer diameter of the device driver being substantially equal to the outer thread diameter of the anchor, such that the proximal end of the suture anchor is received within the cylindrical body of substantially constant outer diameter.

2. A method for installing an appliance through tissue and into bone using a hollow grasping means having jaws, the method comprising the steps of:

(a) grasping the tissue with between the jaws of the hollow grasping means;

(b) introducing the appliance to the tissue through the hollow grasping means;

(c) installing the appliance through the tissue and into the bone; and (d) removing the hollow grasping means from the repair site, leaving the appliance installed in the bone.

3. The method of claim 2, further comprising the step of delivering the hollow grasping means to the tissue through a portal.

4. The method of claim 2, wherein the step of installing the appliance into the bone includes the step of rotating the suture anchor with a power drill and a device driver.

5. The method of claim 2, wherein the appliance comprises a suture anchor, and the method further comprises the step of threading the suture anchor with suture prior to the step of introducing the suture anchor to the tissue.

6. The method of claim 5, wherein the step of installing the suture anchor through the tissue and into the bone comprises the steps of:

(a) coupling a proximal end of the suture anchor to a device driver;

(b) threading the suture from the suture anchor through the device driver;

(c) inserting the threaded device driver and the suture anchor through the hollow grasping means;

(d) attaching a power drill to the proximal end of the device driver; and (e) installing the suture anchor through the tissue and into the bone by rotating the suture anchor with the power drill into the bone.

7. The method of claim 6, wherein the step of threading the suture from the suture anchor through the device driver is performed using a threading device.

8. The method of claim 2, further comprising the step of attaching suture to the appliance.

9. The method of claim 8, further comprising the step of threading the suture through a cannulated driver and coupling the appliance with the driver to form an assembly.

10. The method of claim 9, wherein the step of threading the suture through the cannulated driver is performed using a threading device.

11. The method of claim 9, wherein the step of introducing the appliance to the tissue comprises inserting the assembly into the hollow grasping means.

12. The method of claim 2, wherein the step of introducing the appliance to the tissue comprises introducing the appliance through the jaws of the hollow grasping means.

13. A method for installing an appliance through tissue and into bone using a hollow grasping means, the method comprising the steps of:

(a) grasping the tissue with the hollow grasping means;

(b) introducing the appliance to the tissue through the hollow grasping means;

(c) installing the appliance through the tissue and into the bone by rotating the suture anchor with a power drill and a device driver; and (d) removing the hollow grasping means from the repair site, leaving the appliance in the bone.

14. The method of claim 3, further comprising the step of delivering the hollow grasping means to the tissue through a portal.

15. The method of claim 13, further comprising the step of attaching suture to the appliance.

16. The method of claim 15, further comprising the step of threading the suture through a cannulated driver and coupling the appliance with the driver to form an assembly.

17. The method of claim 16, wherein the step of threading the suture through the cannulated driver is performed using a threading device.

18. The method of claim 16, wherein the step of introducing the appliance to the tissue comprises inserting the assembly into the hollow grasping means.

19. A method for installing a suture anchor through tissue and into bone using a hollow grasping means having jaws, the method comprising the steps of:

(a) grasping the tissue between the jaws of the hollow grasping means;

(b) threading the suture anchor with suture;

(c) introducing the suture anchor to the tissue through the hollow grasping means;

(d) installing the suture anchor through the tissue and into the bone; and (e) removing the hollow grasping means from the repair site, leaving the suture anchor installed in the bone.

20. The method of claim 19, wherein the step of installing the suture anchor through the tissue and into the bone comprises the steps of:

(i) coupling a proximal end of the suture anchor to a device driver;

(ii) threading the suture from the suture anchor through the device driver;

(iii) inserting the threaded device driver and the suture anchor through the hollow grasping means;

(iv) attaching a power drill to the proximal end of the device driver; and (v) installing the suture anchor through the tissue and into the bone by rotating the suture anchor with the power drill and the device driver.

21. The method of claim 20, wherein the suture is threaded from the suture anchor through the device driver using a threading device.

22. The method of claim 19, wherein the step of introducing the appliance to the tissue comprises introducing the appliance through the jaws of the hollow grasping means.

\* \* \* \* \*